United States Patent
Patterson et al.

(10) Patent No.: US 11,097,601 B2
(45) Date of Patent: Aug. 24, 2021

(54) SCENT WARMER

(71) Applicants: Merrium Patterson, Poughkeepsie, NY (US); Anthony Patterson, Poughkeepsie, NY (US)

(72) Inventors: Merrium Patterson, Poughkeepsie, NY (US); Anthony Patterson, Poughkeepsie, NY (US)

(*) Notice: Subject to any disclaimer, the term of this patent is extended or adjusted under 35 U.S.C. 154(b) by 81 days.

(21) Appl. No.: 16/277,700

(22) Filed: Feb. 15, 2019

(65) Prior Publication Data

US 2020/0262271 A1 Aug. 20, 2020

Related U.S. Application Data

(63) Continuation-in-part of application No. 15/238,726, filed on Aug. 17, 2016, now abandoned.

(51) Int. Cl.
*B60H 3/00* (2006.01)
*A61L 9/03* (2006.01)
*A61L 9/16* (2006.01)

(52) U.S. Cl.
CPC ............ *B60H 3/0007* (2013.01); *A61L 9/032* (2013.01); *A61L 9/035* (2013.01); *A61L 9/16* (2013.01); *A61L 2209/10* (2013.01)

(58) Field of Classification Search
CPC ....... B60H 3/0007; A61L 9/032; A61L 9/035; A61L 2209/10; A61L 9/16; G06F 3/0488
See application file for complete search history.

(56) References Cited

U.S. PATENT DOCUMENTS

| | | | |
|---|---|---|---|
| 6,514,467 B1* | 2/2003 | Bulsink | A61L 9/12 239/54 |
| 8,662,480 B1* | 3/2014 | Irvin | B60H 3/0028 261/26 |
| 10,413,630 B1* | 9/2019 | Hsiao | A61L 9/122 |
| 2005/0001337 A1* | 1/2005 | Pankhurst | A61L 9/04 261/104 |
| 2011/0038761 A1* | 2/2011 | Saleh | A61L 9/122 422/124 |
| 2014/0133841 A1* | 5/2014 | Hsiao | A61L 9/03 392/386 |
| 2016/0089466 A1* | 3/2016 | McMinn | C11C 5/002 422/4 |
| 2016/0195257 A1* | 7/2016 | Hsiao | F21S 8/035 362/92 |
| 2017/0112955 A1* | 4/2017 | Bourne | B60H 3/00 |

OTHER PUBLICATIONS

Ametherm (Year: 0).*
Battery University (Year: 2016).*

* cited by examiner

*Primary Examiner* — Sean E Conley
*Assistant Examiner* — Brendan A Hensel
(74) *Attorney, Agent, or Firm* — Johan Eide; Christopher Pilling; My Patent Guys

(57) ABSTRACT

An improved portable scent warmer having a modular or compartmentalized housing holding a scented member, a heating element imparting heat to the scented member to release its fragrance, a fan element for direct the dispersion of the fragrance, a input device for selectively controlling and actuating the heating element; a rotatable cover adjoined to the housing; and at least one power supply means for powering the heating element.

13 Claims, 9 Drawing Sheets

SCENT WARMER

RELATED APPLICATIONS

This application is a continuation-in-part application of non-provisional patent application U.S. Ser. No. 15/238,726 filed on Aug. 17, 2016, the disclosure of which is hereby incorporated in their entirety at least by reference.

BACKGROUND

1. Field of the Invention

The present invention relates to an improved scent warmer for releasing a fragrance. More particularly, the invention relates to a portable scent warmer for use in an automobile for releasing a fragrance.

2. Description of Related Art

A variety of portable scent warmers, including warmers for melting candles or wax having an aromatic scent or fragrance, exist for use in releasing a fragrance inside an automobile. Some of these warmers are battery operated or powered by the automobile's cigarette lighter outlet, and often have an internal heating element which warms or melts an aromatic member to release an aroma, fragrance, or other scent into the immediate atmosphere.

Some heating elements consume a large amount of power when heating the aromatic member and cannot be operated for prolonged use. The ability to tilt these scent warmers in a particular direction for releasing the fragrance can also be problematic. Some scent warmers have a housing that must remain in a fixed in its original horizontal or vertical orientation to prevent spillage after the aromatic member melts. It can also be difficult and time consuming to clean up the melted, hardened aromatic member the housing and car surfaces.

U.S. Patent Application Publication Nos. 2014/0129892 and 2014/0133841 filed by Hsiao disclose an aroma diffuser having a hollow housing, a heat conduction container, a resistor, a plugging device, an aroma capsule, film, and a sealing cover. The heat conducting container is placed inside the housing, with the resistor located under the heat conduction container. The aroma capsule includes an aroma material, such as a scented wax block. The wax block is placed inside a disposable, aluminum foil container. The sealing cover and a film prevent the melted wax from spilling if the device is tilted. The plugging device may be a USB device or cigarette lighter.

U.S. Pat. No. 6,197,263 issued to Blount discloses an automobile air freshener that uses a heating element to warm and melt scented wax for aroma dispersal. The device includes a housing, a base-power unit, a heating element, a replaceable gel-scented cartridge, and a power supply. The power supply is located in the base unit of the device. The power supply may be a cigarette lighter, a battery, or a solar/electric cell. The housing unit has vent slots for the aroma to disperse through.

U.S. Pat. No. 6,249,645 issued to Smith discloses a scent device adapted for use in a vehicle. The device includes a bowl, a scent supply, a cover, and a heating element for melting the scent supply. The bowl has a cavity to hold a scent supply, such as a wax base. The cover has several holes to allow scent vapors to escape. The heating element is adapted for use with a cigarette lighter in an automobile.

U.S. Pat. No. 8,772,675 issued to Juarez discloses a scent warmer for use in a vehicle. The device includes a housing, a heating element, a scented material, and electrical components for powering and illuminating the device.

Problems remain concerning the aromatic or scented member melting and spilling from the container if the container is rotated or tilted. Remnants from the melted scented member may also clog the container's air vents or film. Other problems include a scent warmer lacking a suitable holder that is selectively rotatable without the melted scented member spilling from the housing while still effectively releasing a fragrance, a scent warmer being controlled either manually or wirelessly.

The references do not disclose, teach, or suggest combining or modifying the elements of those references to create an improved scent warmer having a compartmentalized holder for holding a heating element and a scented member, with the holder being selectively rotatable within a handle, and powered by at least power supply means.

A need exists for an improved scent warmer having a holder for holding a scented member and a heating element, with the holder having a vent with a plurality of slots to allow a fragrance or aroma to release into the atmosphere.

A need exists for an improved scent warmer having a holder designed to prevent leakage or spillage of a dissolved or melted scented member.

A need exists for an improved scent warmer having at least one power supply means for powering the warmer having a heating element that melts the scented member to release a fragrance.

A need exists for an improved scent warmer having a handle that supports a holder, with the holder being selectively rotatable therein to a desired orientation then secured in place. It is desirable to provide an improved scent warmer that resolves the problems noted in the references.

SUMMARY

It is an object of the invention to provide an improved scent warmer that is easy to assembly, and that is safe to use and operate in an automobile or in any other location capable of working with the scent warmer's power supply means.

It is another object of the invention to provide an improved scent warmer that has a replaceable scented member that is long lasting, yet easily removable for cleaning the scent warmer's surfaces.

It is yet another object of the invention to provide an improved scent warmer that has more than one option for a power supply, including, but not limited to, drawing power from an automobile's cigarette lighter, an external USB connection, or a battery.

It is an object of the invention to provide an improved scent warmer for heating a scented member with a heating element, with the scent warmer being enclosed within a compartmentalized holder to prevent spilling of the melted scented member if the orientation of the holder is changed.

It is an object of the invention to provide an improved scent warmer having a rotatable cover, with the rotatable cover having a plurality of holes to allow a fragrance or aroma to release into the atmosphere. The rotatable cover allowing the user to manually rotate the rotatable cover to an upward or downward position based on the desired fragrance level of the user.

In order to do so, an improved scent warmer is provided comprising a housing having a right ride, a left side, a top side, a bottom side, a proximal end, and a distal end, wherein the distal end is adjoined to a power outlet and the proximal end having at least one opening to allow a scent to disperse outside the housing. Secondly, a first plurality of holes positioned on the housing, each hole of the first plurality of holes adapted to receive a fastener. A heating element is adjoined to the bottom side of the housing followed by a fan element adjoined to the housing to circulate air heated by the heating element. On the outside of the housing, a rotatable cover having a second plurality of holes, is adjoined to the housing. The rotatable cover allows a limited volume of air to circulate outside the housing. A power supply for the scent warmer, wherein the power supply is adjoined to the distal end of the housing. An input device accessible from the outside of the housing is included, wherein the input device is configured to receive an input. An electrical control assembly regulates the circulated air and temperature, wherein the electrical control assembly is connectively coupled to the power supply. Additionally, a plurality of resistors are located inside the scent warmer, wherein the plurality of resistors is communicatively connected to the electrical control assembly. The plurality of resistors configured to monitor and control a temperature within the housing. Lastly, a scented member provides a source of fragrance, wherein the scented member is heated by the heating element to disperse a scent and wherein the fan element is configured to circulate the scent away from the housing.

BRIEF DESCRIPTION OF THE FIGURES

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF CERTAIN EMBODIMENTS

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise. Any reference to "or" herein is intended to encompass "and/or" unless otherwise stated.

As used herein, the term "about" refers to an amount that is near the stated amount by about 0%, 5%, or 10%, including increments therein.

Unless otherwise defined, all technical terms used herein have the same meaning as commonly understood by one of ordinary skill in the art to which this disclosure belongs.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

Figure 1:
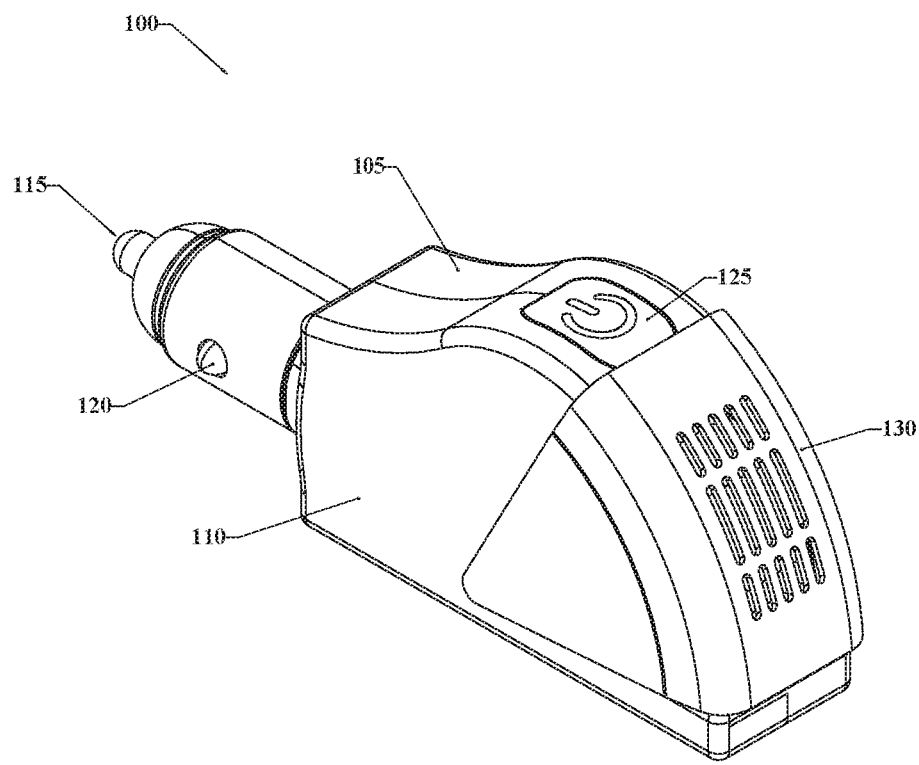
FIG. 1 shows an exemplary isometric perspective view of one embodiment of the scent warmer.

FIG. 1 shows an exemplary isometric perspective view of one embodiment of the scent warmer 100. In the current exemplary embodiment, the scent warmer is contained within a housing having a left housing panel 110 and a right housing panel 105. The housing having a right side, a left side, a top side, a bottom side, a proximal end, and a distal end 140, wherein the distal end is adjoined to a power outlet and the proximal end having at least one opening to allow a scent to disperse outside the housing. The scent warmer housing is formed, in some embodiments, by adjoining the left housing panel 110 and a right housing panel 105. The adjoining, in some embodiments, is carried out by a first plurality of holes 145, wherein the first plurality of holes is adapted to receive a fastener. In some embodiments, the adjoining of the left housing panel 110 and right housing panel 105 is carried out by at least one member of a fastener set consisting of: an adhesive, a snap fit, a threaded member, a weld, a magnet, a spring, a ultrasonic weld, a chemical weld. In some embodiments, the housing is one continuous member. In some embodiments, the housing has at least two members that are adjoined to form a housing. The left housing panel and a right housing panel can be made of at least one member of a material set, by way of non-limiting example, including: a metal, a plastic, a wood and a composite material.

In the exemplary embodiment shown in FIG. 1-9, the housing has a right ride, a left side, a top side, a bottom side, a proximal end and a distal end 140. In the current exemplary embodiment, the rotatable cover 130 is adjoined to the proximal end of the scent warmer and comprises a second plurality of holes to allow a scent to disperse and circulate outside the housing. The distal end of the housing, in some embodiments, is circular to adapt to a cigarette lighter output or other round power supply ports know to one skilled in the art. In the current embodiment, the scent warmer comprises a distal end 140 that is circular having a power supply comprising a positive contact 115 and at least one negative contact 120. The positive contact and at least one negative contact arranged to form a closed electrical circuit.

In the exemplary embodiment shown in FIGS. 1-9, the user controls the power supply of the scent warmer 100 by an input device 125. In some embodiments, the input device is connectively coupled to the power supply and controls the power supplied to at least one of the following: an electrical control assembly 155, the positive contact 115, at least one negative contact 120, a heating element 160, a fan element 165. The input device of the current exemplary embodiment allows the user to control the power supplied to the electrical control assembly by means of a push button located upon the top side of the housing. In some embodiments, the input device is at least one member of an input set consisting of: a button, a switch, a dial, a touchscreen, and a potentiometer. The electrical control assembly controls at least one of a control set consisting of: amperage, voltage, polarity, and any digital aspect supplied by the power supply to at least one of the following: the heating element, the fan element and the input device. In some embodiments, the input device further comprises illuminating means. In some embodiments, the input device is of a wireless embodiment having a wireless connectively via a communication network. Examples of a communication network include, by way of non-limiting example, any of the following: WiFi, RF, cellular, Bluetooth, LoRa, WLAN, or microwave methods. For instance, the input device 125 can optionally communicates with a remote computer system of a user. Examples of remote computer systems include personal computers (e.g., portable PC), slate or tablet PCs (e.g., Apple® iPad, Samsung® Galaxy Tab, etc.), smartphones (e.g., Apple® iPhone, Android-enabled device, Blackberry®, etc.), or personal digital assistants. In some embodiments, the electrical control assembly of the scent warmer is communicatively coupled to the communication network and the remote computer system.

Figure 2:
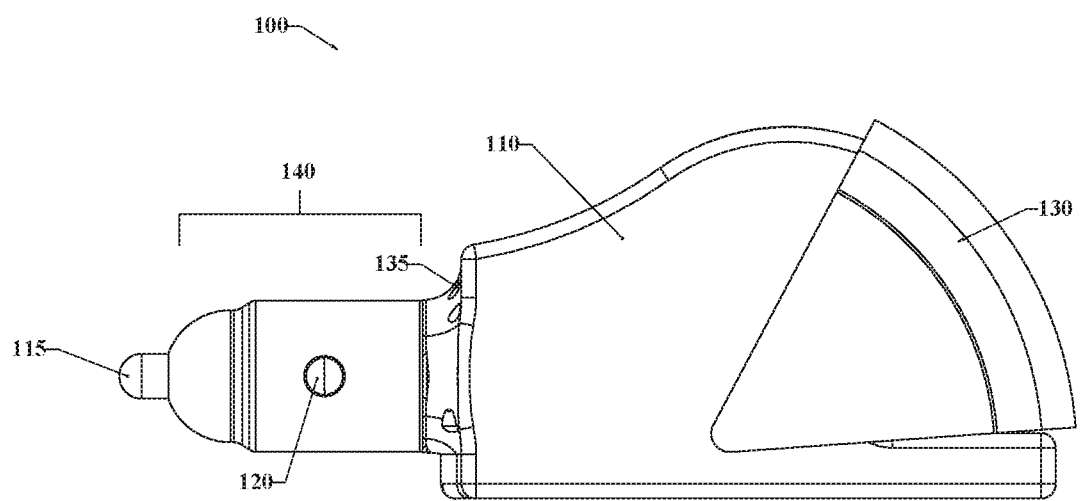
FIG. 2 shows an exemplary left perspective view of one embodiment of the scent warmer.

FIG. 2 shows an exemplary left perspective view of one embodiment of the scent warmer 100. The rotatable cover 130 is shown in a downward position in resting contact with the housing. The rotatable cover has a second plurality of holes to allow a heated fragrance to disperse outside the housing. In some embodiments, the rotatable cover has no holes and is a solid member sealing fragrance within the housing. The rotatable cover is rotated, in the current exemplary embodiment, upward along an axis perpendicular the right side and the left side of the housing. The rotatable cover, resting in an upward position is therefore resting in contact with the top side of the housing and in doing so, allows all scent and air to circulate away from the housing freely.

Figure 3:
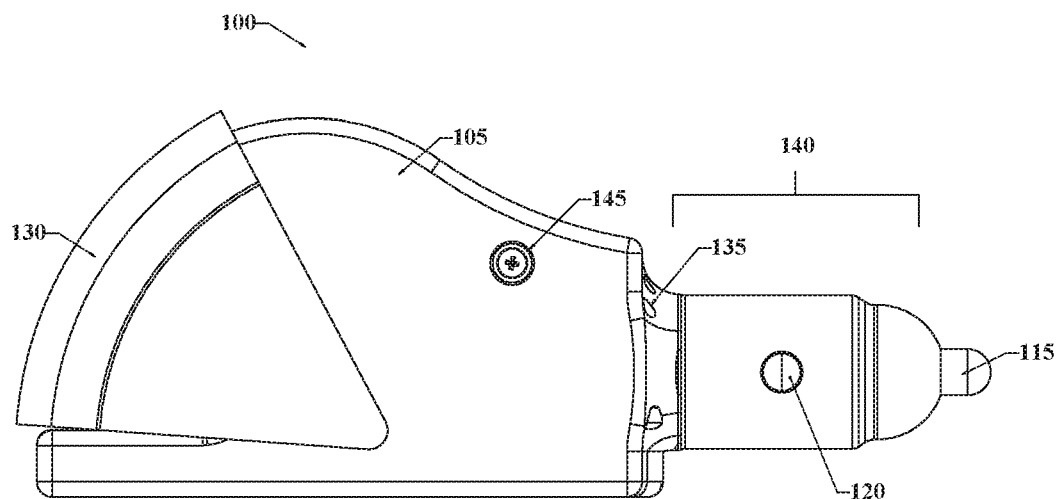
FIG. 3 shows an exemplary right view of one embodiment of the scent warmer.

FIG. 3 shows an exemplary right view of one embodiment of the scent warmer. FIG. 3 illustrates the first plurality of holes 145 adjoining the left housing panel 110 and a right housing panel 105. The housing of the scent warmer, in the current exemplary embodiment, includes a fourth plurality of holes 135, wherein the fourth plurality of holes allows air to enter the housing. In some embodiments, the fourth plurality of holes 135 are replaced with a series of openings to allow air to enter the housing. In some embodiments, the fourth plurality of holes 135 may further comprise a filter to control the air particle size allowed to enter the housing.

Figure 4:
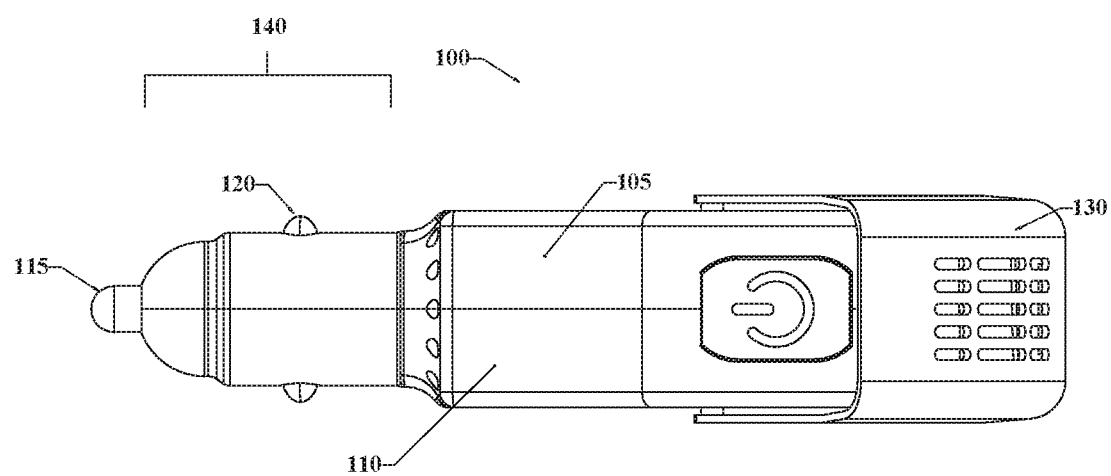
FIG. 4 shows an exemplary top view of one embodiment of the scent warmer.
Figure 5:
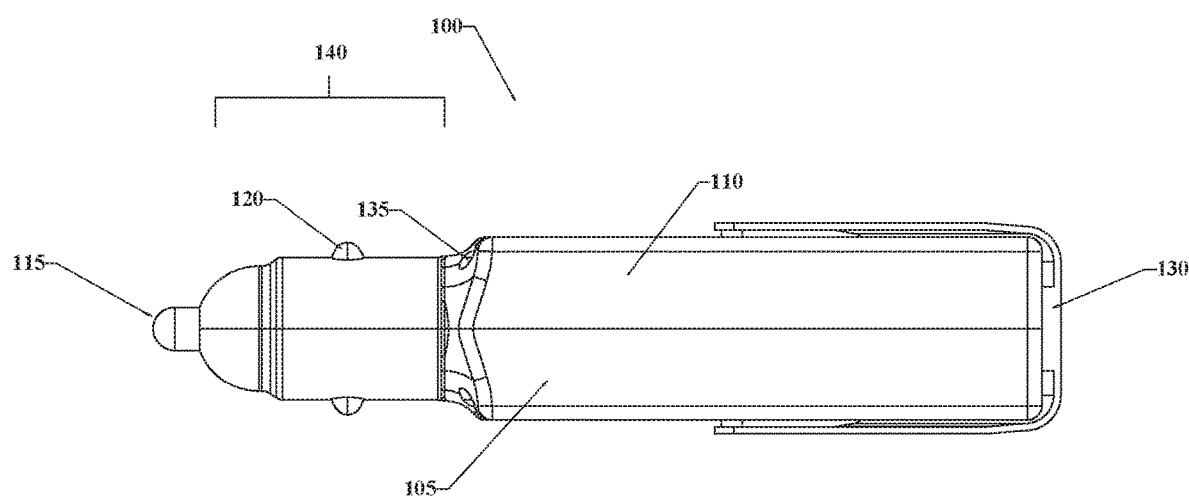
FIG. 5 shows an exemplary bottom view of one embodiment of the scent warmer.

FIG. 4 shows an exemplary top view of one embodiment of the scent warmer. FIG. 5 shows an exemplary bottom view of one embodiment of the scent warmer. The positive contact and at least one negative contact are shown located on the distal end of the housing and are arranged for the user to insert the distal end into a power supply port, such as a cigarette lighter. In some embodiments, the power supply is at least one member of a power set consisting of: a USB port, a cigarette lighter port, an AC/DC outlet and a battery. In some embodiments, the battery is selected from one member of a battery set consisting of: a lithium-ion battery, a nickel metal hydride battery, a nickel-cadmium cell battery, a capacitor energy storage pack, and a mechanical energy storage.

Figure 6:
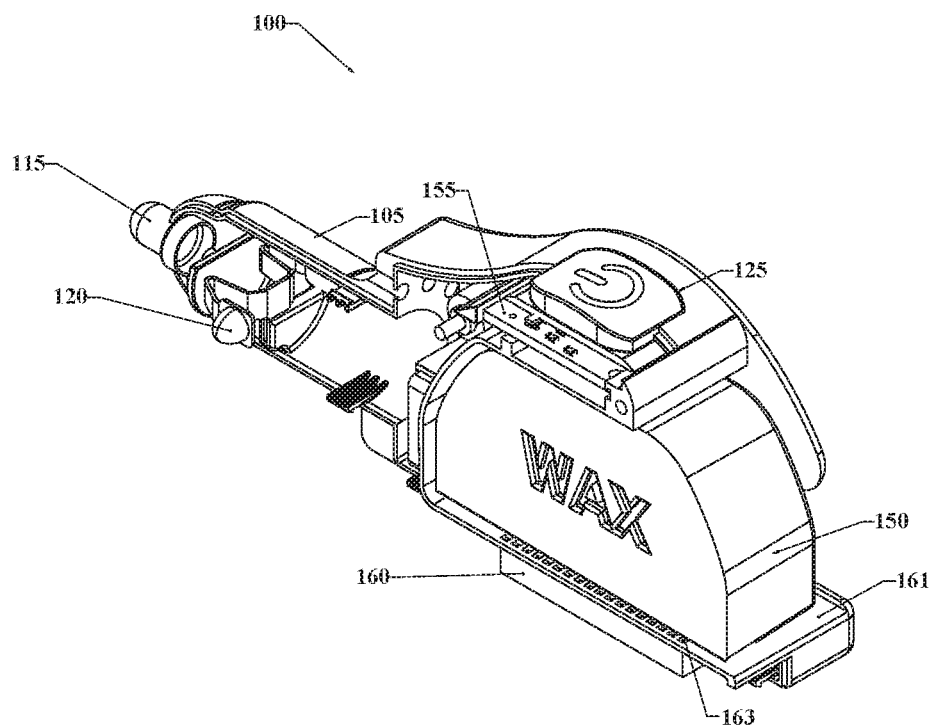
FIG. 6 shows an exemplary isometric perspective view of one embodiment of the scent warmer with a portion of the exemplary housing hidden from view.

FIG. 6 shows an exemplary isometric perspective view of one embodiment of the scent warmer with a portion of the left housing panel 110 hidden from view. With the left housing panel hidden from view, the heating element, in a current exemplary embodiment, is shown located alongside the bottom side of the housing. The heating element is controlled by the electrical control assembly 155 located alongside the top of the housing in the current exemplary embodiment. In the current embodiment, alongside the heating element an insulating pad member 161 is shown located between a scented member 150 and the heating element 160. The insulating pad member serves as a physical and thermal barrier between the heating element and scented member, therein limiting the rate of heat transfer between the heating element and the scented member. In some embodiments, a plurality of resistors is located within the housing, wherein the plurality of resistors is communicatively connected to the electrical control assembly. The plurality of resistors configured to monitor a temperature within the housing. In some embodiments, the resistors measure a change in resistance and therein temperature at specific locations within the housing. In some embodiments, the resistor is in contact with the heating element. In some embodiments, the insulating pad member further comprises a third plurality of holes 163, the third plurality of holes allowing heat to disperse directly from the heating member to the scented member. In other embodiments, the third plurality of holes can further comprise a series of openings. In some embodiments, the insulating pad member further comprise a convex face to aide in retaining melted scented members within the housing of the scent warmer. In some embodiments, the bottom side of the housing further comprises a cupped shape configured to retain the scented member inside the housing during heating. In some embodiments, the insulating pad member comprises a metal plate.

Figure 7:
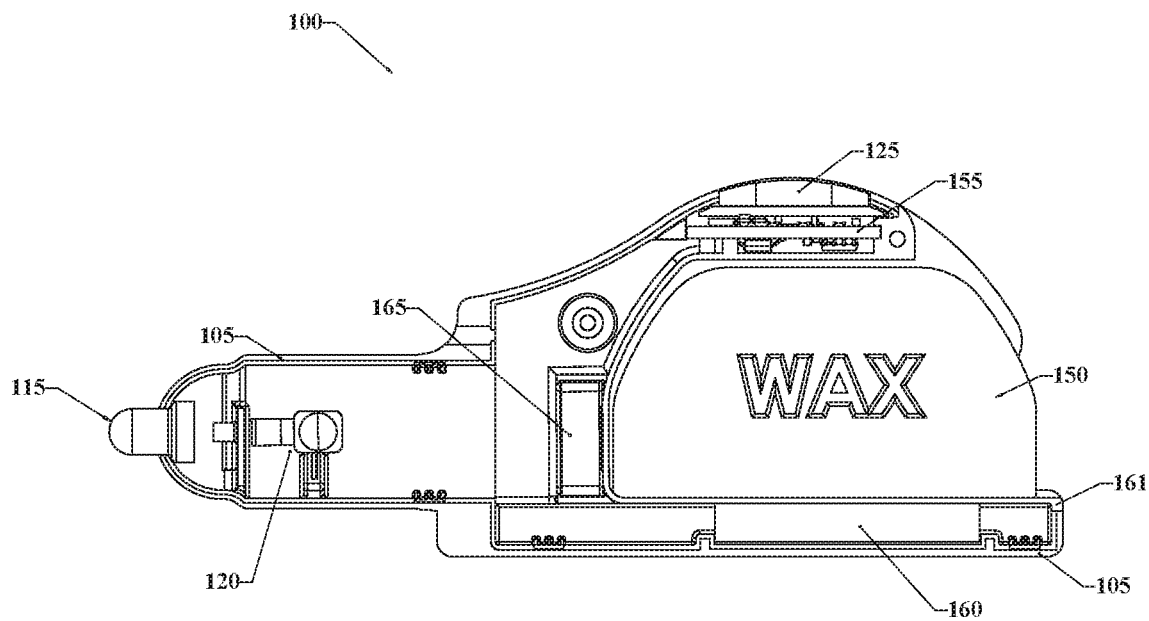
FIG. 7 shows an exemplary left view of one embodiment of the scent warmer with a portion of the exemplary housing hidden from view.

FIG. 7 shows an exemplary left view of one embodiment of the scent warmer with a portion of the exemplary housing hidden from view. The scented member 150 of the scent warmer further comprises a plurality of scented members. The scented member 150 may be any substance having, or being infused with, a fragrance or aroma convertible from a solid form or a semi-solid form to a liquid form or a gaseous form when heated or warmed. In some embodiments, the scented member is made of at least one member of a scented materials set, by way of non-limiting example, including: a wax material, an aroma compound, a plant material, an essential oil, a synthetic oil, a seed oil, a naturally occurring oil, and an isoprene compound.

Figure 8:
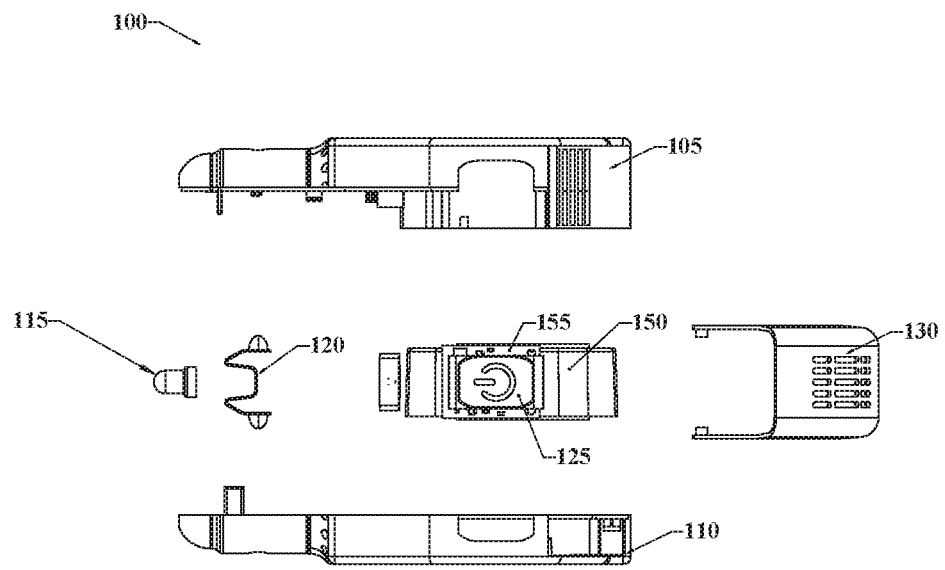
FIG. 8 shows an exemplary exploded top view of one embodiment of the scent warmer.
Figure 9:
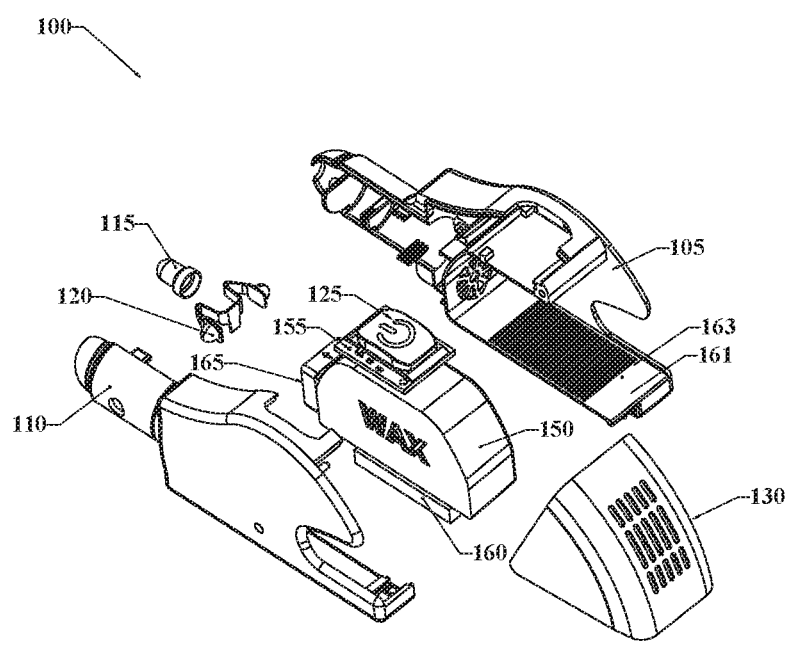
FIG. 9 shows an exemplary exploded isometric view of one embodiment of the scent warmer.

FIG. 8-9 shows an exemplary exploded top view of one embodiment of the scent warmer. In some embodiments, the rotatable cover 130 further comprises a sliding cover, wherein the sliding cover moves in a linear direction to allow the scent to disperse outside the housing.

Any element in a claim that does not explicitly state "means for" performing a specified function, or "step for" performing a specified function, is not to be interpreted as a "means" or "step" clause as specified in 35 U.S.C. § 112, ¶6. In particular, any use of "step of" in the claims is not intended to invoke the provision of 35 U.S.C. § 112, ¶ 6.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A scent warmer comprising:
a housing having a right side, a left side, a top side, a bottom side, a proximal end, and a distal end, wherein the distal end is adjoined to a power outlet and the proximal end having at least one opening to allow a scent to disperse outside the housing;
a heating element adjoined to the bottom side of the housing;
a fan element adjoined to the housing;
a u-shaped rotatable cover having a back surface and opposing side walls protruding from the back surface, wherein the rotatable cover is hingedly adjoined to the housing and pivots along an axis perpendicular the right side and the left side of the housing;
a power supply, wherein the power supply is adjoined to the distal end of the housing;
an input device, wherein the input device is configured to receive an input;
an electrical control assembly, wherein the electrical control assembly is connectively coupled to the power supply;
a plurality of resistors, wherein the plurality of resistors is communicatively connected to the electrical control assembly, the plurality of resistors configured to monitor a temperature within the housing;
a scented member positioned within the housing, wherein the scented member is heated by the heating element to disperse a scent and wherein the fan element is configured to circulate the scent away from the housing.

2. The scent warmer of claim 1, wherein the electrical control assembly controls at least one of a control set consisting of: amperage, voltage, polarity, and any digital aspect supplied by the power supply.

3. The scent warmer of claim 1, wherein the input device is at least one member of an input set consisting of: a button, a switch, a dial, a touchscreen, and a potentiometer.

4. The scent warmer of claim 1, wherein the housing further comprises an insulating pad member positioned between the heating element and the scented member, wherein the insulating pad member aides in distributing heat from the heating element to the scented member.

5. The scent warmer of claim 1, wherein the input device further comprises illuminating means.

6. The scent warmer of claim 1, wherein the power supply is at least one member of a power set consisting of: a USB port, a cigarette lighter port, an AC/DC outlet and a battery.

7. The scent warmer of claim 6, wherein the battery is selected from one member of a battery set consisting of: a lithium-ion battery, a nickel metal hydride battery, a nickel-cadmium cell battery, a capacitor energy storage pack, and a mechanical energy storage.

8. The scent warmer of claim 1, wherein the scent warmer further comprises a plurality of scented members.

9. The scent warmer of claim 1, wherein the bottom side of the housing further comprises a cupped shape configured to retain the scented member inside the housing during heating.

10. The scent warmer of claim 4, wherein the insulating pad member further comprises a third plurality of holes, the third plurality of holes allowing heat to disperse directly from the heating member to the scented member.

11. The scent warmer of claim 1, wherein the housing further comprises a fourth plurality of holes located on the housing, the fourth plurality of holes allowing air to enter the housing.

12. The scent warmer of claim 1, wherein the housing further comprises a first plurality of holes positioned on the housing, each hole of the first plurality of holes adapted to receive a fastener.

13. The scent warmer of claim 1, wherein the u-shaped rotatable cover further comprises a second plurality of holes protruding through the rotatable cover.

* * * * *